(12) United States Patent
Zhao et al.

(10) Patent No.: US 9,366,642 B2
(45) Date of Patent: Jun. 14, 2016

(54) BACK SCATTERING INSPECTION SYSTEMS FOR HUMAN BODY

(71) Applicants: Nuctech Company Limited, Haidian District, Beijing (CN); Tsinghua University, Haidian District, Beijing (CN)

(72) Inventors: Ziran Zhao, Beijing (CN); Zhiqiang Chen, Beijing (CN); Yuanjing Li, Beijing (CN); Wanlong Wu, Beijing (CN); Ming Ruan, Beijing (CN); Yinong Liu, Beijing (CN); Yingkang Jin, Beijing (CN); Le Tang, Beijing (CN); Yanjie Wen, Beijing (CN); Xiuwei Chen, Beijing (CN); Fuhua Ding, Beijing (CN); Bin Sang, Beijing (CN); Zongjun Shen, Beijing (CN)

(73) Assignees: Nuctech Company Limited, Haidian District, Beijing (CN); Tsinghua University, Haidian District, Beijing (CN)

( * ) Notice: Subject to any disclaimer, the term of this patent is extended or adjusted under 35 U.S.C. 154(b) by 83 days.

(21) Appl. No.: 14/135,840

(22) Filed: Dec. 20, 2013

(65) Prior Publication Data

US 2014/0185769 A1  Jul. 3, 2014

(30) Foreign Application Priority Data

Dec. 27, 2012 (CN) .......................... 2012 1 0581690

(51) Int. Cl.
*G01N 23/203* (2006.01)
*G01T 1/167* (2006.01)
(Continued)

(52) U.S. Cl.
CPC ............ *G01N 23/203* (2013.01); *A61B 6/4021* (2013.01); *A61B 6/4266* (2013.01); *A61B 6/483* (2013.01); *G01T 1/167* (2013.01); *G01V 5/0025* (2013.01)

(58) Field of Classification Search
CPC . G01N 23/203; G01V 5/0025; A61B 6/4021; A61B 6/4266; A61B 6/483
See application file for complete search history.

(56) References Cited

U.S. PATENT DOCUMENTS

| 5,307,396 A | 4/1994 | Tsuchino |
| 6,094,472 A | 7/2000 | Smith |

(Continued)

FOREIGN PATENT DOCUMENTS

| CN | 100377690 C | 4/2008 |
| CN | 101918820 A | 12/2010 |

(Continued)

OTHER PUBLICATIONS

Extended European Search Report for corresponding European Patent Application No. 13198326.4 mailed Apr. 25, 2014.

(Continued)

*Primary Examiner* — Glen Kao
*Assistant Examiner* — Chih-Cheng Kao
(74) *Attorney, Agent, or Firm* — Merchant & Gould P.C.

(57) ABSTRACT

A human body back-scattering inspection system is disclosed. The system comprises a flying-spot forming unit configured to output beams of X-rays, a plurality of discrete detectors which are arranged vertically along a human body to be inspected, and a controlling unit coupled to the flying-spot forming unit and the plurality of detectors, and configured to generate a control signal to control the flying-spot forming unit and the plurality of detectors to perform a partition synchronous scan on the human body to be inspected vertically. The present disclosure utilizes the geometry property of the human body back-scattering inspection system, and proposes a multiple-point synchronous scan mechanism which largely accelerates the inspection of human body.

9 Claims, 2 Drawing Sheets

(51) Int. Cl.
*G01V 5/00* (2006.01)
*A61B 6/00* (2006.01)

(56) References Cited

U.S. PATENT DOCUMENTS

| | | |
|---|---|---|
| 6,151,381 A | 11/2000 | Grodzins et al. |
| 2003/0016790 A1 | 1/2003 | Grodzins et al. |
| 2004/0228442 A1* | 11/2004 | Sakaguchi et al. ............... 378/87 |
| 2009/0116617 A1* | 5/2009 | Mastronardi et al. ........... 378/87 |
| 2011/0274249 A1* | 11/2011 | Gray et al. ....................... 378/87 |
| 2012/0307967 A1 | 12/2012 | Smith |

FOREIGN PATENT DOCUMENTS

| | | |
|---|---|---|
| CN | 101960333 A | 1/2011 |
| CN | 201974533 U | 9/2011 |
| CN | 202110297 U | 1/2012 |
| CN | 102540268 A | 7/2012 |
| CN | 102565110 A | 7/2012 |
| CN | 203012153 U | 6/2013 |
| EP | 2 703 849 A1 | 3/2014 |
| WO | WO 2009/067394 A2 | 5/2009 |
| WO | WO 2012/088810 A1 | 7/2012 |

OTHER PUBLICATIONS

United Kingdom Combined Search and Examination Report for corresponding United Kingdom Patent Application No. GB1322302.9 mailed Mar. 13, 2014.

Chinese Office Action for corresponding Chinese Patent Application No. 201210581690.5 mailed Jan. 25, 2016.

* cited by examiner

BACK SCATTERING INSPECTION SYSTEMS FOR HUMAN BODY

This application claims benefit of Serial No. 201210581690.5, filed 27 Dec. 2012 in China and which application is incorporated herein by reference. To the extent appropriate, a claim of priority is made to each of the above disclosed applications.

TECHNICAL FIELD

The present disclosure generally relates to radiation imaging techniques, and more particularly, to human body back-scattering inspection systems which are capable of accelerating the security inspection.

BACKGROUND

The existing X-ray human body back-scattering scanning and inspecting apparatus normally uses a single-point scanning method, which uses a relatively large-scale back-scattering detector. The technique uses a longitudinal scanning manner where X-ray machine and detector move up and down in synchronization, or a scanning manner where the X-ray machine rotates coaxially (or translates) while the detector moves laterally. Only one beam of light irradiates on a surface of the human body at a time whatever manner is used. Therefore, it is concerned in the technical field how to accelerate the scanning without degrading image quality and enhancing the irradiation dose on the human body.

SUMMARY

In view of the problem of the prior art that the scanning speed is low, embodiment of the present disclosure provides human body back-scattering inspection systems which are capable of accelerating the security inspection.

According to an aspect of the disclosure, there is provided a human body back-scattering inspection system comprising a flying-spot forming unit configured to output beams of X-rays; a plurality of discrete detectors which are arranged vertically along a human body to be inspected; and a controlling unit coupled to the flying-spot forming unit and the plurality of detectors and configured to generate a control signal to control the flying-spot forming unit and the plurality of detectors to perform a partition synchronous scan on the human body to be inspected vertically.

According to embodiments of the present disclosure, the flying-spot forming unit generates respective beams of X-rays for a plurality of vertical parts of the human body to be inspected, so that synchronous scan for different parts is performed on the human body to be inspected vertically.

According to embodiments of the present disclosure, the human body to be inspected is divided into an upper part and a lower part vertically, and the plurality of discrete detectors includes a first detector and a second detector that are arranged from top to bottom. When a first beam of X-rays scans the upper part, a second beam of X-rays scans the lower part, and the first detector receives a first reflected beam of X-rays and the second detector receives a second reflected beam of X-rays.

According to embodiments of the present disclosure, the human body to be inspected is divided into an upper part and a lower part vertically, and the plurality of discrete detectors include a first detector and a second detector that are arranged from top to bottom. When a second beam of X-rays scans the upper part, a first beam of X-rays scans the lower part, and the first detector receives a second reflected beam of X-rays and the second detector receives a first reflected beam of X-rays.

According to embodiments of the disclosure, the human body to be inspected is divided into an upper part and a lower part vertically, and the plurality of discrete detectors includes a first detector, a second detector and a third detector that are arranged from top to bottom. When a first beam of X-rays scans the upper part and a second beam of X-rays scans the lower part, a value detected by the first detector is taken as a value of the first reflected beam of X-rays, and a sum of values detected by the second and third detectors is taken as a value of the second reflected beam of X-rays. When the first beam of X-rays scans the lower part and the second beam of X-rays scans the upper part, a sum of values detected by the first and second detectors is taken as a value of the second reflected beam of X-rays, and a value detected by the third detector is taken as a value of the first reflected beam of X-rays.

According to embodiments of the disclosure, the human body to be inspected is divided into an upper part and a lower part vertically, and the plurality of discrete detectors include a first detector, a second detector, a third detector and a fourth detector that are arranged from top to bottom. The upper part includes a first sub-part, a second sub-part and a third sub-part. When a first beam of X-rays scans the first sub-part, a value detected by the first detector is taken as a value of the first reflected beam of X-rays, and a sum of values detected by the second detector, the third detector and the fourth detector is taken as a value of the second reflected beams of X-rays. When a first beam of X-rays scans the second sub-part, a sum of values detected by the first detector and the second detector is taken as a value of the first reflected beam of X-rays, and a sum of values detected by the third detector and the fourth detector is taken as a value of the second reflected beams of X-rays. When a first beam of X-rays scans the third sub-part, a sum of values detected by the first detector, the second detector and the third detector is taken as a value of the first reflected beam of X-rays, and a value detected by the fourth detector is taken as a value of the second reflected beams of X-rays.

According to embodiments of the present disclosure, the flying-spot forming unit has a plurality of holes spirally distributed on a surface of its cylinder, which are configured to output the first beam of X-rays and the second beam of X-rays in a time-sharing manner, where the time for outputting the first beams of X-rays and the time for outputting the second beam of X-rays are different by a half of a cycle of intensity of beams varying over time.

According to embodiments of the present disclosure, the flying-spot forming unit includes a first flying-spot forming unit and a second flying-spot forming unit arranged along the vertical direction of the human body to be inspected, which are configured to independently scan the upper part and lower part of the human body to be inspected.

According to embodiments of the present disclosure, the first flying-spot forming unit and the second flying-spot forming unit scan the human body to be inspected in the same direction, and have the same scanning speed.

According to the foregoing embodiments of the disclosure, a plurality of human body scanning devices perform a partition scan on a human body at the same time, and thus a multiple-point synchronous scan is achieved and it largely accelerates the inspection of human body.

BRIEF DESCRIPTION OF THE DRAWINGS

The implementations of the disclosure are illustrated in the drawings. The drawings and implementations provide some embodiments of the disclosure non-exclusively without limitation, where.

DETAILED DESCRIPTION OF THE EMBODIMENTS

Figure 1:
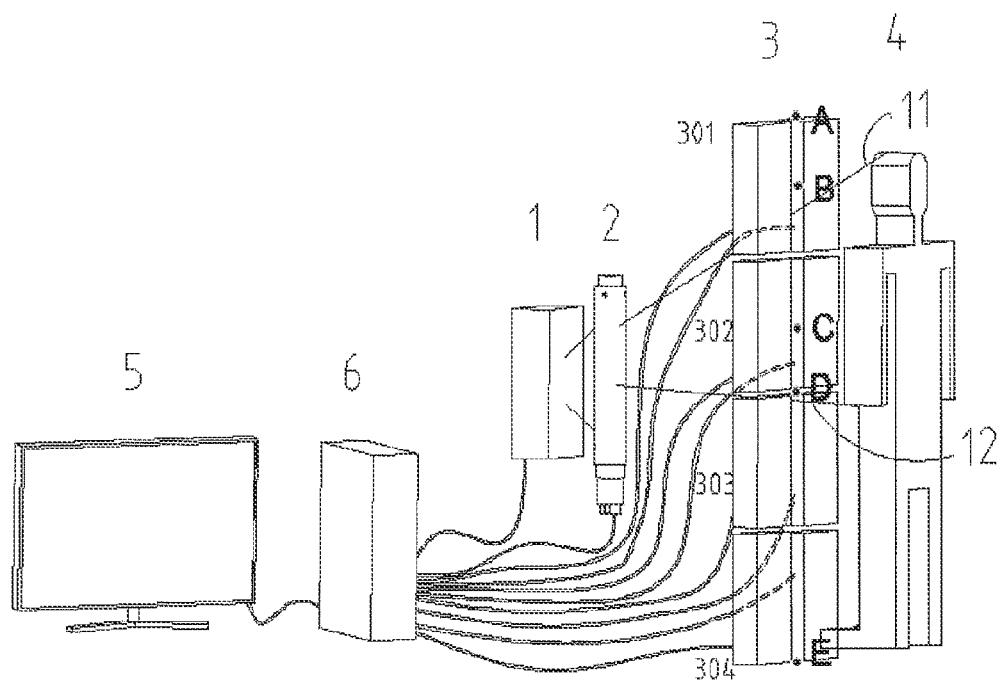
FIG. 1 illustrates a schematic diagram of a human body back-scattering system according to an embodiment of the disclosure.

The particular embodiments of the disclosure are described below in details. It shall be noted that the embodiments herein are used for illustration only, but not limiting the disclosure. In the description below, a number of particular details are explained to provide a better understanding to the disclosure. However, it is apparent to those skilled in the art the disclosure can be implemented without these particular details. In other examples, well known circuits, materials or methods are not described so as not to obscure the disclosure.

Throughout the specification, the reference to "one embodiment," "an embodiment," "one example" or "an example" means that the specific features, structures or properties described in conjunction with the embodiment or example are included in at least one embodiment of the present disclosure. Therefore, the phrases "in one embodiment," "in an embodiment," "in one example" or "in an example" occurred at various positions throughout the specification may not refer to one and the same embodiment or example. Furthermore, specific features, structures or properties may be combined into one or several embodiments or examples in any appropriate ways. Moreover, it should be understood by those skilled in the art that the term "and/or" used herein means any and all combinations of one or more listed items.

In view of the problem of the prior art that the scanning speed is low, the embodiment of the present disclosure provides a human body back-scattering inspection system. In the system, a flying-spot forming unit outputs beams of X-rays. A plurality of discrete detectors is arranged vertically along a human body to be inspected. A controlling unit is coupled to the flying-spot forming unit and the plurality of detectors, and configured to generate a control signal to control the flying-spot forming unit and the plurality of detectors to perform vertically a partition synchronous scan on the human body to be inspected. In such way, the plurality of beams of X-rays outputted from the flying-spot forming unit scan a plurality of parts of the human body synchronously, and thereby the scanning speed is enhanced.

For example, the flying-spot forming unit generates respective beams of X-rays for a plurality of vertical parts of the human body to be inspected (for example, upper part and lower part), and the plurality of discrete detectors include a first detector and a second detector that are arranged from top to bottom. For example, when a first beam of X-rays scans the upper part, a second beam of X-rays scans the lower part, and the first detector receives a first reflected beam of X-rays and the second detector receives a second reflected beam of X-rays. Take another example, when a second beam of X-rays scans the upper part, a first beam of X-rays scans the upper part, the first detector receives a second reflected beam of X-rays and the second detector receives a first reflected beam of X-rays.

In other embodiments, the human body to be inspected is divided into an upper part and a lower part vertically, and the plurality of discrete detectors includes a first detector, a second detector and a third detector that are arranged from top to bottom. In such case, when a first beam of X-rays scans the upper part and a second beam of X-rays scans the lower part, a value detected by the first detector is taken as a value of the first reflected beam of X-rays, and a sum of values detected by the second and third detectors is taken as a value of the second reflected beam of X-rays. When the first beam of X-rays scans the lower part and the second beam of X-rays scans the upper part, a sum of values detected by the first and second detectors is taken as a value of the second reflected beam of X-rays, and a value detected by the third detector is taken as a value of the first reflected beam of X-rays.

In other embodiments, the human body to be inspected is divided into an upper part and a lower part vertically, and the plurality of discrete detectors includes a first detector, a second detector, a third detector and a fourth detector that are arranged from top to bottom. In such case, the upper part includes a first sub-part, a second sub-part and a third sub-part. When a first beam of X-rays scans the first sub-part, a value detected by the first detector is taken as a value of the first reflected beam of X-rays, and a sum of values detected by the second detector, the third detector and the fourth detector is taken as a value of the second reflected beams of X-rays. When a first beam of X-rays scans the second sub-part, a sum of values detected by the first detector and the second detector is taken as a value of the first reflected beam of X-rays, and a sum of values detected by the third detector and the fourth detector is taken as a value of the second reflected beams of X-rays. When a first beam of X-rays scans the third sub-part, a sum of values detected by the first detector, the second detector and the third detector is taken as a value of the first reflected beam of X-rays, and a value detected by the fourth detector is taken as a value of the second reflected beams of X-rays.

The above division of the human body is given as an example. It can be anticipated by those skilled in the art to divide the human body into more parts vertically. Furthermore, in the foregoing examples, the use of the terms "upper part" and "lower part" does not mean that the human body is divided into two equal parts. In other words, the lengths of the upper part and the lower part may be the same or different.

FIG. 1 illustrates a schematic diagram of a human body back-scattering inspection system according to an embodiment of the disclosure. As shown in FIG. 1, the system employs a common lateral translation scanning manner. The system comprises an X-ray machine and beam collimator 1, a drum flying-spot unit 2, a back-scattering detector 3, an inspection interface 5, and a signal collecting and processing unit 6. The human body of to-be-inspected object 4 is under a partition scan process. The X-ray machine and stream collimator 1 and the drum flying-spot unit 2 may rotate coaxially (or translate) and back-scattering detector 3 may translates laterally, so that beams of flying-spots scan up and down.

Figure 2:
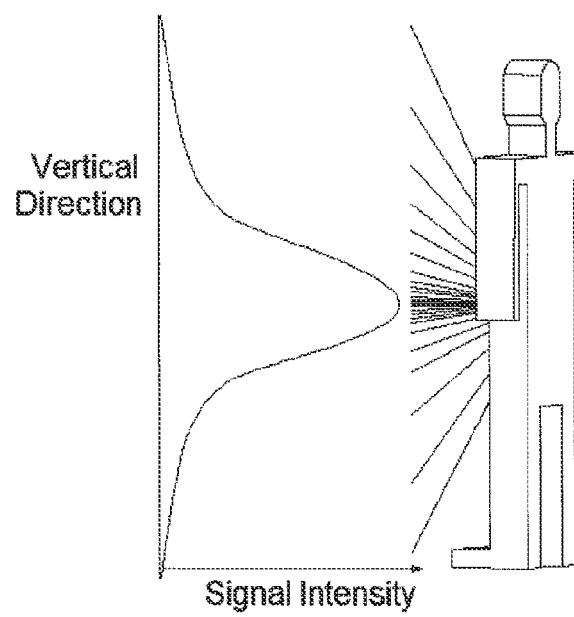
FIG. 2 illustrates a diagram of distribution of intensity of scattered signals along the vertical direction of the human body in a human body back-scattering inspection process.

As shown in FIG. 1, detector 3 includes discrete detectors 301, 302, 303 and 304 that are arranged from up to down. In general, back-scattering detector 3 and human body 4 are so close to each other that intensity of back-scattered X-rays changes largely along the vertical direction of the human body, as shown in FIG. 2. Therefore, the back-scattering detector is partitioned into a plurality of discrete detectors 301 to 304. The intensities of signals received by a back-scattering detector near the target and by a back-scattering detector far away from the target differ largely. In view of such case, a plurality of scanning points is provided with a certain spacing for synchronous scanning, and a plurality of back-scattering detectors independently collects data.

In some embodiments, a two-point synchronous scan process is taken as an example to be described in details. The human body is divided into an upper part and a lower part accordingly. Four discrete groups of detectors 301, 302, 303 and 304 are arranged vertically. Two scanning beams 11 and 12 (shown in FIG. 1) are separated by a half of the height of the human body. For example, when the first scanning beam 11 is at point A, the second scanning beam 12 is just at point D, and they have the same scanning speed and direction. In other words, when the first scanning beam 11 scans from point A to point D, the second scanning beam 12 exactly scans from point D to point E; and when the first scanning beam 11 scans from point D to point E, the second scanning beam 12 returns to point A and scans from point A to point D. The signal collection is performed as follows. When the first scanning beam 11 scans from point A to point D, signal of detector 301 is due to the first beam 11, and signals of detectors 302, 303 and 304 are due to the second beam 12; when the first scanning beam 11 scans from point B to point C, signals of detectors 301 and 302 are due to the first beam 11, and signals of detectors 303 to and 304 are due to the second beam 12; when the first scanning beam 11 scans from point C to point D, signals of detectors 301, 302 and 303 are due to the first beam 11, and signal of detector 304 is due to second beam 12, and so on. In a real application, partition of the detector and processing of signals may be different as long as a multiple-point synchronous scan can be implemented without affecting quality of the scanning image.

According to some embodiments, the flying-spot forming unit has a plurality of holes spirally distributed on a surface of its cylinder, which are configured to output a plurality of beams of X-rays (e.g., the first beam of X-rays and the second beam of X-rays) in a time-sharing manner, where the time for outputting the first beams of X-rays and the time for outputting the second beam of X-rays are different by a half of a cycle of the intensity of beams varying over time.

Figure 3:
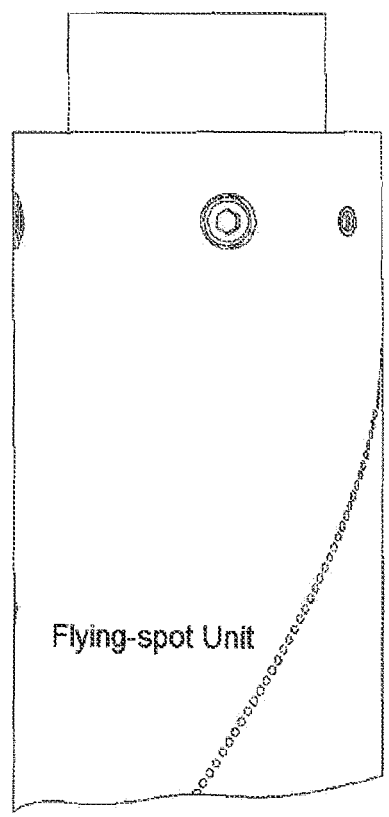
FIG. 3 illustrates a schematic diagram of a flying-spot forming unit used in a human body back-scattering inspection system according to another embodiment of the disclosure.

As an example of a human body back-scattering inspection system, if the flying-spot unit generates discontinuous beams (i.e., the beams of flying-spots appear to be the dots shown in FIG. 3), the dots of scanning beams have a beam-free interval therebetween, and the embodiments of the present disclosure may use the condition to have two beams alternatively and synchronously scan. That is, when one beam is emitting beams, the other beam is in a shield state, so that signal interference between two beams can be reduced to the best, and thus a two-beam synchronous scan can be implemented.

Figure 4:
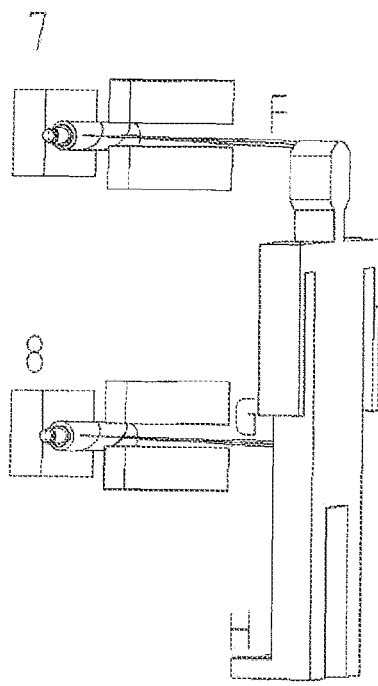
FIG. 4 illustrates a schematic diagram of a human body back-scattering inspection system according to still another embodiment of the disclosure.

In other embodiments, the flying-spot forming unit may include a first flying-spot forming unit and a second flying-spot forming unit that arranged along the vertical direction of the human body to be inspected, which are configured to independently scan the upper part and lower part of the human body to be inspected. In such case, the first flying-spot forming unit and the second flying-spot forming unit scan the human body to be inspected in the same direction, and have the same scanning speed. FIG. 4 illustrates a schematic diagram of a human body back-scattering inspection system according to still another embodiment of the disclosure. FIG. 4 shows a human body vertical scanning manner. A plurality of sets of X-ray machine and back-scattering detector are provided to perform multiple-point synchronous scanning for respective parts. As for the number of parts, it can be selected so that signal interference between adjacent parts will not impact the image quality and index.

Take two-point synchronous scanning as an example. The system includes two sets of devices 7 and 8, each set including an X-ray machine, a flying-spot unit and a detector. Each flying-spot unit scans one part. The sets are as far as possible from each other, and have the same scanning speed and direction, so as to reduce information interference to each other. That is, when device 7 scans from point F to point G, device 8 just scans from point G to point H, and two sets of devices are only responsible for their own scanning parts.

The foregoing detailed description has set forth various embodiments of the human body back-scattering inspection system via the use of block diagrams, flowcharts, and/or examples. Insofar as such block diagrams, flowcharts, and/or examples contain one or more functions and/or operations, it will be understood by those skilled in the art that each function and/or operation within such examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of those skilled in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

While the present disclosure has been described with reference to several typical embodiments, it is apparent to those skilled in the art that the terms are used for illustration and explanation purpose and not for limitation. The present disclosure may be practiced in various forms without departing from the esprit or essence of the disclosure. It should be understood that the embodiments are not limited to any of the foregoing details, and shall be interpreted broadly within the esprit and scope as defined by the following claims. Therefore, Modifications and alternatives falling within the scope of the claims and equivalents thereof are to be encompassed by the scope of the present disclosure which is defined by the claims as attached.

What is claimed is:

1. A human body back-scattering inspection system comprising:
    a flying-spot forming unit configured to output beams of X-rays;
    a plurality of detectors arranged discrete from each other vertically along a human body to be inspected, wherein the human body is vertically divided into a plurality of parts corresponding to the plurality of detectors; and
    a controlling unit coupled to the flying-spot forming unit and the plurality of detectors, and configured to generate a control signal to control the flying-spot forming unit and the plurality of detectors to scan the plurality of parts of human body to be inspected vertically and synchronously.

2. The human body back-scattering inspection system according to claim 1, wherein the flying-spot forming unit generates respective beams of X-rays for a plurality of vertical parts of the human body to be inspected, so that synchronous scan for different parts is performed on the human body to be inspected vertically.

3. The human body back-scattering inspection system according to claim 2, wherein the human body to be inspected is divided into an upper part and a lower part vertically, and the plurality of detectors includes a first detector and a second detector that are arranged discretely from top to bottom,
    wherein when a first beam of X-rays scans the upper part, a second beam of X-rays scans the lower part, and the first detector receives a first reflected beam of X-rays and the second detector receives a second reflected beam of X-rays.

4. The human body back-scattering inspection system according to claim 2, wherein the human body to be inspected is divided into an upper part and a lower part vertically, and the plurality of detectors includes a first detector and a second detector that are arranged discretely from top to bottom,
    wherein when a second beam of X-rays scans the upper part, a first beam of X-rays scans the lower part, and the first detector receives a second reflected beam of X-rays and the second detector receives a first reflected beam of X-rays.

5. The human body back-scattering inspection system according to claim 2, wherein the human body to be inspected is divided into an upper part and a lower part vertically, and the plurality of detectors include a first detector, a second detector and a third detector that are arranged discretely from top to bottom,
    wherein when a first beam of X-rays scans the upper part and a second beam of X-rays scans the lower part, a value detected by the first detector is taken as a value of the first reflected beam of X-rays, and a sum of values detected by the second and third detectors is taken as a value of the second reflected beam of X-rays, and
    wherein when the first beam of X-rays scans the lower part and the second beam of X-rays scans the upper part, a sum of values detected by the first and second detectors is taken as a value of the second reflected beam of X-rays, and a value detected by the third detector is taken as a value of the first reflected beam of X-rays.

6. The human body back-scattering inspection system according to claim 2, wherein the human body to be inspected is divided into an upper part and a lower part vertically, and the plurality of detectors include a first detector, a second detector, a third detector and a fourth detector that are arranged discretely from top to bottom,
    wherein the upper part includes a first sub-part, a second sub-part and a third sub-part, and wherein when a first beam of X-rays scans the first sub-part, a value detected by the first detector is taken as a value of the first reflected beam of X-rays, and a sum of values detected by the second detector, the third detector and the fourth detector is taken as a value of the second reflected beams of X-rays,
    wherein when a first beam of X-rays scans the second sub-part, a sum of values detected by the first detector and the second detector is taken as a value of the first reflected beam of X-rays, and a sum of values detected by the third detector and the fourth detector is taken as a value of the second reflected beams of X-rays, and
    wherein when a first beam of X-rays scans the third sub-part, a sum of values detected by the first detector, the second detector and the third detector is taken as a value of the first reflected beam of X-rays, and a value detected by the fourth detector is taken as a value of the second reflected beams of X-rays.

7. The human body back-scattering inspection system according to claim 2, wherein the flying-spot forming unit has a plurality of holes spirally distributed on a surface of its cylinder, which are configured to output the first beam of X-rays and the second beam of X-rays in a time-sharing manner, and wherein the time for outputting the first beams of X-rays and the time for outputting the second beam of X-rays are different by a half of a cycle of intensity of beams varying over time.

8. The human body back-scattering inspection system according to claim 1, wherein the flying-spot forming unit includes a first flying-spot forming unit and a second flying-spot forming unit arranged along the vertical direction of the human body to be inspected, which are configured to independently scan the upper part and lower part of the human body to be inspected.

9. The human body back-scattering inspection system according to claim 8, wherein the first flying-spot forming unit and the second flying-spot forming unit scan the human body to be inspected in the same direction, and have the same scanning speed.

* * * * *